US010231602B2

(12) United States Patent
Tago (10) Patent No.: US 10,231,602 B2
(45) Date of Patent: Mar. 19, 2019

(54) VIDEO PROCESSOR FOR PROCESSING A VIDEO SIGNAL INPUT

(71) Applicant: OLYMPUS CORPORATION, Hachioji-shi, Tokyo (JP)

(72) Inventor: Hiroki Tago, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/611,073

(22) Filed: Jun. 1, 2017

(65) Prior Publication Data

US 2017/0265716 A1 Sep. 21, 2017

Related U.S. Application Data

(63) Continuation of application No. PCT/JP2016/069029, filed on Jun. 27, 2016.

(30) Foreign Application Priority Data

Aug. 4, 2015 (JP) .................................. 2015-154291

(51) Int. Cl.
*G06F 11/00* (2006.01)
*A61B 1/00* (2006.01)
(Continued)

(52) U.S. Cl.
CPC ...... *A61B 1/00009* (2013.01); *A61B 1/00006* (2013.01); *A61B 1/04* (2013.01); *A61B 1/045* (2013.01)

(58) Field of Classification Search
CPC ... G06F 2009/4557; G06F 2009/45575; G06F 2009/45591; G06F 2009/5077;
(Continued)

(56) References Cited

U.S. PATENT DOCUMENTS 8,896,680 B2 * 11/2014 Okawa ..................... A61B 1/04
348/76
9,699,509 B2 * 7/2017 Tago .................. H04N 21/4437
(Continued)

FOREIGN PATENT DOCUMENTS

JP 2010-004979 A 1/2010
JP 2011-244884 A 12/2011
(Continued)

OTHER PUBLICATIONS

Sep. 20, 2016 International Search Report issued in Patent Application No. PCT/JP2016/069029.
(Continued)

*Primary Examiner* — Elmira Mehrmanesh
(74) *Attorney, Agent, or Firm* — Oliff PLC (57) ABSTRACT

A video processor distributes hardware resources and software resources related to video signal processing performed by a video signal processing unit to a first partition and a second partition, assigns minimal processing from among the video signal processing to the resources distributed to the first partition, assigns processing from among the video signal processing that is other than the minimal processing to the resources distributed to the second partition, monitors anomalies in the resources distributed to the first partition and the second partition, and only resets resources distributed to a partition in which an anomaly has been detected by the monitoring.

6 Claims, 3 Drawing Sheets

(51) Int. Cl.
*A61B 1/04* (2006.01)
*A61B 1/045* (2006.01)

(58) Field of Classification Search
CPC .............. G06F 11/0712; G06F 11/301; G06F 11/1438; G06F 11/1441
See application file for complete search history.

(56) References Cited

U.S. PATENT DOCUMENTS

| | | | | |
|---|---|---|---|---|
| 2011/0242300 | A1* | 10/2011 | Hashimoto | H04N 5/23203 348/65 |
| 2013/0013953 | A1* | 1/2013 | Eck | G06F 9/45545 714/2 |
| 2013/0176410 | A1* | 7/2013 | Takahashi | A61B 1/045 348/65 |
| 2014/0249523 | A1* | 9/2014 | Odell | A61B 18/1233 606/35 |
| 2015/0082082 | A1 | 3/2015 | Hirano | |
| 2016/0004600 | A1 | 1/2016 | Eiro et al. | |
| 2016/0309983 | A1* | 10/2016 | Suzuki | A61B 1/00006 |

FOREIGN PATENT DOCUMENTS

| | | |
|---|---|---|
| JP | 2013-225208 A | 10/2013 |
| JP | 2014-059733 A | 4/2014 |
| JP | 2014-115703 A | 6/2014 |

OTHER PUBLICATIONS

Sep. 20, 2016 Written Opinion of the International Searching Authority issued in Patent Application No. PCT/JP2016/069029.
Mar. 7, 2017 Office Action issued in Japanese Patent Application No. 2016-563481.
Jan. 17, 2017 Office Action issued in Japanese Patent Application No. 2016-563481.

* cited by examiner

VIDEO PROCESSOR FOR PROCESSING A VIDEO SIGNAL INPUT

CROSS-REFERENCE TO RELATED APPLICATIONS

This application is based upon and claims the benefit of priority of the prior Japanese Patent Application No. 2015-154291, filed Aug. 4, 2015, the entire contents of which are incorporated herein by reference.

This is a Continuation Application of PCT Application No. PCT/JP2016/069029, filed Jun. 27, 2016, which was not published under PCT Article 21(2) in English.

FIELD

The present invention relates to a video processor that includes a video signal processing unit that processes a video signal input from an endoscope.

BACKGROUND

There has been a conventional system that includes a plurality of control devices. A CPU (central processing unit), a microcontroller, an FPGA (field-programmable gate array), and a SoC (system-on-a-chip) are examples of the control device.

In the system described above, the plurality of control devices are engaged in operating the system while sharing processing with one another. Thus, even if an anomaly has occurred in (a problem has occurred with) one of the plurality of control devices, it is possible to keep an operation of the system performed with the other control devices in a normal state.

In recent years, with the development of multicore or many-core processors, there has emerged a high-power and high-performance control device, which makes it possible to provide a configuration in which the overall operation of a system is controlled using one high-power and high-performance control device.

In the conventional system, when an anomaly has occurred in a control device, the control device is restored by resetting the control device. Resetting performed using a watchdog is its typical example.

An endoscopic system is known that includes a processor device including a CPU that functions as, for example, a DIP (digital image processing circuit), an anomaly detection circuit, an initialization circuit, and an alternative DIP (see, for example, Japanese Laid-open Patent Publication No. 2010-4979). In the processor device included in the endoscopic system, when the anomaly detection circuit has detected an anomaly in the DIP, the initialization circuit outputs a reset signal to the DIP and the CPU in which the DIP is in operation is reset. Then, the alternative DIP performs image processing until the DIP is restarted, and the DIP restarts the image processing after the DIP is restarted. Further, an endoscopic device is also known in which a processor device having this configuration is configured using a well-known virtual technology (see, for example, Japanese Laid-open Patent Publication No. 2010-4979). In this endoscopic device, the processor device includes hardware resources, a hypervisor, a first OS (operation system), a second OS, and a third OS. The configuration is made such that software that corresponds to the DIP described above operates on the first OS, software that corresponds to the alternative DIP described above operates on the second OS, and software that operates as the anomaly detection circuit and the initialization circuit described above operates on the third OS.

SUMMARY

A video processor according to an aspect of the present invention includes: a video signal processing unit that processes a video signal input from an endoscope; a distribution unit that distributes hardware resources and software resources related to video signal processing performed by the video signal processing unit to a first partition and a second partition; a first assignment unit that assigns minimal processing from among the video signal processing to the resources distributed to the first partition; a second assignment unit that assigns processing from among the video signal processing that is other than the minimal processing to the resources distributed to the second partition; a monitoring unit that monitors anomalies in the resources distributed to the first partition and the second partition; and a resetting unit that only resets resources distributed to a partition in which an anomaly has been detected by the monitoring unit.

DESCRIPTION OF EMBODIMENTS

Embodiments of the present invention will now be described with reference to the drawings.

Figure 1:
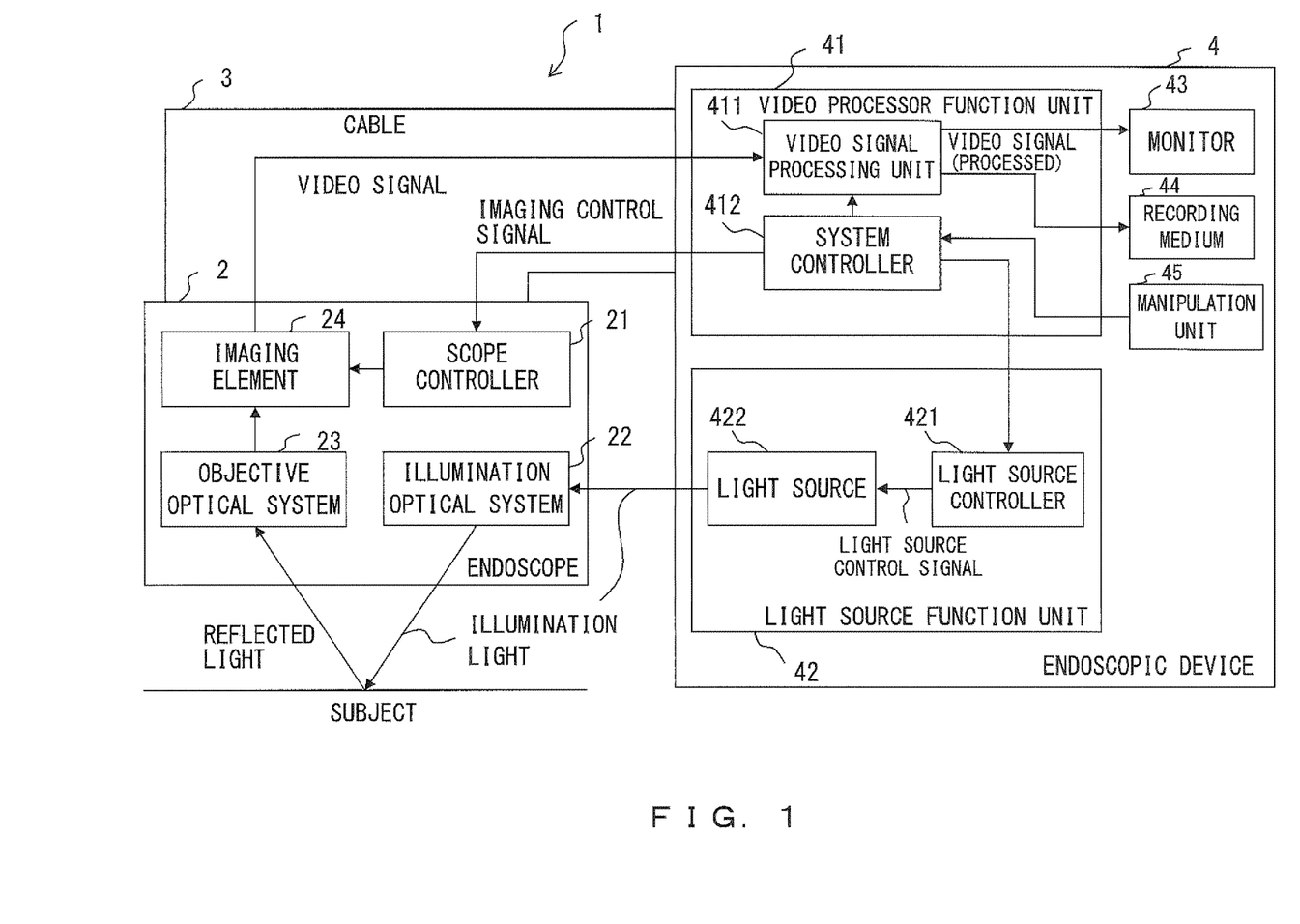
FIG. 1 illustrates an example of a configuration of an endoscopic system that includes a video processor according to an embodiment.

FIG. 1 illustrates an example of a configuration of an endoscopic system that includes a video processor according to an embodiment of the present invention. This endoscopic system is used for an endoscopic examination or the like in a medical institution (such as a hospital).

As illustrated in FIG. 1, an endoscopic system 1 includes an endoscope 2, a cable 3, and an endoscopic device 4, and has a configuration in which the endoscope 2 is connected to the endoscopic device 4 through the cable 3.

The endoscope 2 is an endoscope having a flexible inserted portion (a flexible endoscope), and includes a scope controller 21, an illumination optical system 22, an objective optical system 23, and an imaging element 24. The scope controller 21 controls the imaging element 24 according to an imaging control signal input from a system controller 412 (described later) of a video processor function unit 41 of the endoscopic device 4 through the cable 3. The illumination optical system 22 illuminates, onto a subject (such as an observation region in the body cavity), illumination light emitted from a light source 422 (described later) of a light source function unit 42 of the endoscopic device 4 and guided through a light guide (not illustrated). The objective optical system 23 forms an image of reflected light from the subject (reflected light of the illumination light illuminated onto the subject) on an imaging surface of the imaging element 24. Under the control of the scope controller 21, the imaging element 24 converts a subject image (the reflected light from the subject) formed on the imaging surface into a video signal that is an electric signal, and outputs the video signal to a video signal processing unit 411 (described later) of the video processor function unit 41 of the endoscopic device 4 through the cable 3.

The cable 3 includes a signal line that transmits a signal (such as a video signal and an imaging control signal) transmitted and received between the endoscope 2 and the endoscopic device 4.

The endoscopic device 4 includes the video processor function unit 41, the light source function unit 42, a monitor 43, a recording medium 44, and a manipulation unit 45.

The video processor function unit 41 includes the video signal processing unit 411 and the system controller 412.

Under the control of the system controller 412, the video signal processing unit 411 processes a video signal input from the imaging element 24 through the cable 3. The video signal processing unit 411 will be described in detail later using FIG. 2.

The system controller 412 controls each component of the endoscopic system 1 such as the video signal processing unit 411, a light source controller 421 of the light source function unit 42, and the scope controller 21 of the endoscope 2. For example, the system controller 412 performs an initial setting of the video signal processing unit 411 that is a control of the video signal processing unit 411. In this initial setting, hardware resources and software resources related to display video signal processing (described later) performed by the video signal processing unit 411 are distributed to a secure partition and a main partition, and performs processing such as processing of assigning minimal processing from among the display video signal processing to the resources distributed to the secure partition and processing of assigning processing from among the display video signal processing that is other than the minimal processing to the resources distributed to the main partition. Further, the system controller 412 also performs, for example, a control according to a user manipulation received by the manipulation unit 45.

The light source function unit 42 includes the light source controller 421 and the light source 422. Under the control of the system controller 412, the light source controller 421 outputs a light source control signal to the light source 422 so as to control the light source 422. The light source 422 emits illumination light according to a light source control signal input from the light source controller 421.

The monitor 43 displays a video according to a video signal processed by the video signal processing unit 411. The recording medium 44 records the video according to the video signal processed by the video signal processing unit 411. The manipulation unit 45 receives various manipulations from a user and reports the various manipulations to the system controller 412.

In the endoscopic system 1 having the configuration described above, the video processor function unit 41 and the light source function unit 42 may be configured to be one device as illustrated in FIG. 1, or they may be independently of each other. In the latter case, the light source function unit 42 may be provided separately from the endoscopic device 4. Alternatively, the video processor function unit 41 and the light source function unit 42 may be provided, for example, within the endoscope 2, and the endoscope 2, the cable 3, and the endoscopic device 4 may be configured to be one device.

The endoscope 2 is not limited to a flexible endoscope, but it may be, for example, an endoscope having a rigid inserted portion (a rigid endoscope) or an optical endoscope (such as a fiberscope or an optical visual tube for surgery) in which a camera head is connected to an eyepiece of the optical endoscope.

The imaging element 24 may be an image sensor such as a CCD (charge-coupled device) or a CMOS (complementary metal oxide semiconductor).

Further, a method for illuminating illumination light onto a subject may be, for example, a simultaneous lighting or a sequential lighting. Here, the simultaneous lighting is a method for illuminating white light on a subject, and the sequential lighting is a method for sequentially illuminating pieces of light in different wavelength bands (pieces of light of different color components) in a chronological order.

The light source 422 may be, for example, a semiconductor light source or a lamp source. Here, the semiconductor light source may be, for example, a white LED (light emitting diode) that emits white light, or a combination of a plurality of LEDs that each emit light in a different wavelength band (R, G, and B) in which illumination light of a desired color tone is obtained by combining the pieces of light emitted from the respective LEDs, or a laser source. Alternatively, a semiconductor light source that is the light source 422 may be configured to be provided in a tip of the inserted portion of the endoscope 2 when, for example, the endoscope 2, the cable 3, and the endoscopic device 4 are configured to be one device as described above. The lamp source may be, for example, a xenon lamp source or a halogen lamp source.

The configuration may be made such that transmission and reception of a signal between the endoscope 2 and the endoscopic device 4 is performed over a wire as illustrated in FIG. 1, or wirelessly. In the former case, the signal transmitted and received between the endoscope 2 and the endoscopic device 4 is not limited to an electric signal, and it may be, for example, an optical signal. In this case, an electric signal is modulated into an optical signal on the transmission side, and an optical signal is demodulated into an electric signal on the reception side.

The monitor 43 may be, for example, an LCD monitor. Further, the monitor 43 may be configured to be built in within the endoscopic device 4 as illustrated in FIG. 1, or to be external to the endoscopic device 4.

The recording medium 44 may be configured to be built in within the endoscopic device 4 as illustrated in FIG. 1, or it may be a recording medium such as an SD card or a USB (universal serial bus) memory that is removable from the endoscopic device 4. Alternatively, the recording medium 44 may be a recording medium of an external recording device that is a different device than the endoscopic device 4. In this case, the recording medium 44 may be, for example, a recording medium of an external recording device that is local to the endoscopic device 4 without using a network, or a recording medium of an external recording device (such as a server) that is connected to the endoscopic device 4 through the network.

The manipulation unit 45 may be configured to be built in within the endoscopic device 4 as illustrated in FIG. 1, or to be external to the endoscopic device 4. In the former case, the manipulation unit 45 may be, for example, a front panel switch that is provided on a front surface of the endoscopic device 4. In this case, the front panel switch may be, for example, a physical switch, or a virtual switch that is realized by, for example, a touch panel. Further, when the manipulation unit 45 is configured to be external to the endoscopic device 4, the manipulation unit 45 may be, for example, a keyboard connected to the endoscopic device 4, or a scope switch provided in a holding unit of the endoscope 2, or a portable digital assistant (such as a tablet PC (personal computer) and a smartphone) connected to the endoscopic device 4 over a wire, or wirelessly.

Figure 2:
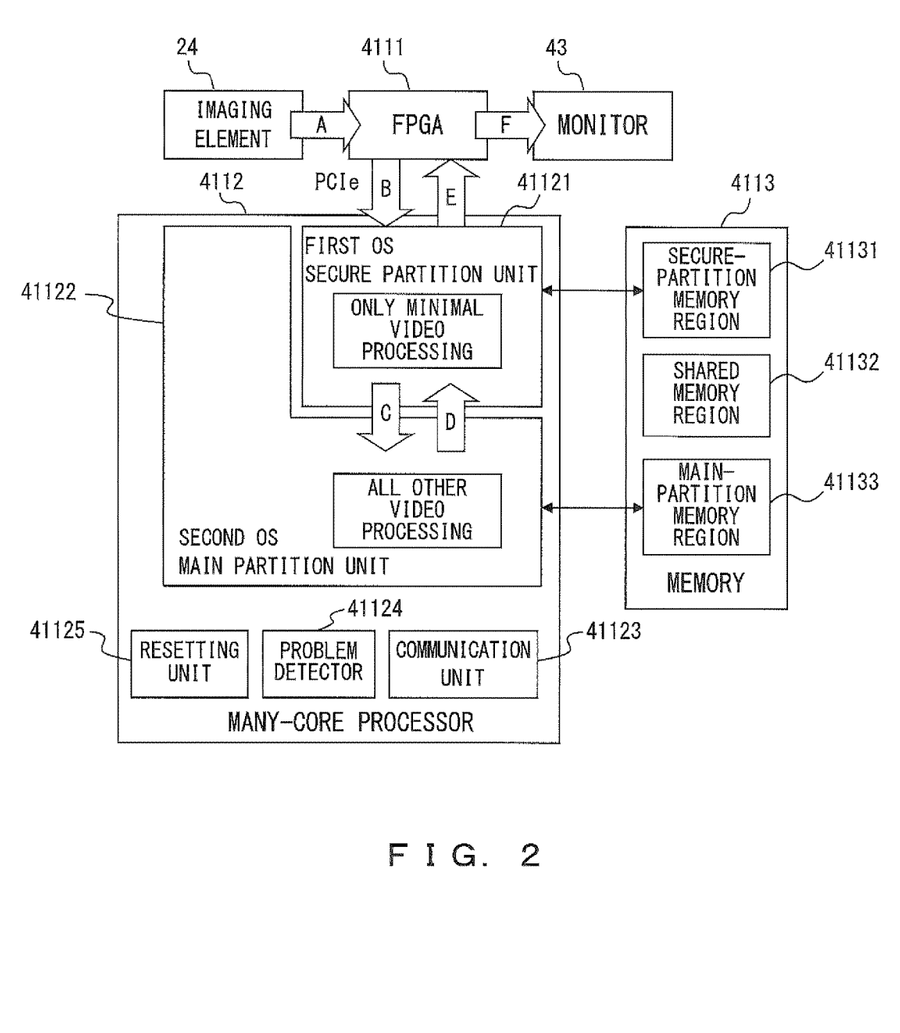
FIG. 2 illustrates an example of an internal configuration of a video signal processing unit according to the embodiment.

FIG. 2 illustrates an example of an internal configuration of the video signal processing unit 411. However, only the components that are primarily related to the display video signal processing performed by the video signal processing unit 411 are illustrated in FIG. 2 as the example of the internal configuration. The display video signal processing is video signal processing performed in order to display a video signal input from the imaging element 24 of the endoscope 2 on the monitor 43.

As illustrated in FIG. 2, the video signal processing unit 411 includes an FPGA 4111, a many-core processor (or a multicore processor) 4112, and a memory 4113.

The FPGA 4111 performs processing including converting a video signal input from the imaging element 24 of the endoscope 2 through the cable 3 into data in a form that can be processed by the many-core processor 4112 (such as data in a PCIe (PCI express) form) and outputting the data to the many-core processor 4112. Further, the FPGA 4111 also performs, for example, processing including converting data input from the many-core processor 4112 into a video signal in a form that can be displayed by the monitor 43 and outputting the data to the monitor 43.

The many-core processor 4112 includes a plurality of core processors (hereinafter simply referred to as "cores"). The plurality of cores are distributed to a plurality of partitions by the system controller 412 performing the initial setting. The plurality of partitions include a secure partition, a main partition, a partition for communication, a partition for problem detection, and a partition for resetting.

In the following descriptions, (one or more) cores distributed to the secure partition are referred to as a secure partition unit 41121. (One or more) Cores distributed to the main partition are referred to as a main partition unit 41122. (One or more) Cores distributed to the partition for communication are referred to as a communication unit 41123. (One or more) Cores distributed to the partition for problem detection are referred to as a problem detector 41124. (One or more) Cores distributed to the partition for resetting are referred to as a resetting unit 41125.

The secure partition unit 41121 and the main partition unit 41122 perform display video signal processing on data input from the FPGA 4111 and performs processing of outputting the processed data to the FPGA 4111. Specifically, the secure partition unit 41121 performs minimal processing from among the display video signal processing. Here, the minimal processing from among the display video signal processing is minimal processing needed to display a video signal input from the imaging element 24 on the monitor 43, and is, for example, processing of converting RAW data into RGB data. The main partition unit 41122 performs processing from among the display video signal processing that is other than the minimal processing. Here, the processing from among the display video signal processing that is other than the minimal processing includes, for example, γ correction processing, white balance processing, noise reduction processing, and enhancement processing.

The communication unit 41123 performs transmission and reception of data between cores that are distributed to different partitions through a shared memory region 41132 (described later) of the memory 4113. For example, the communication unit 41123 performs transmission and reception of data between the secure partition unit 41121 and the main partition unit 41122.

The problem detector 41124 monitors hardware resources and software resources distributed to the secure partition by the system controller 412 performing the initial setting, and hardware resources and software resources distributed to the main partition by the initial setting being performed, so as to detect problems with (anomalies in) the resources.

In the present embodiment, the hardware resources distributed to the secure partition include the secure partition unit 41121 and a secure-partition memory region 41131 (described later). The software resources distributed to the secure partition include a first OS and at least one of a device driver, middleware, and an application that operate on the first OS. The hardware resources distributed to the main partition include the main partition unit 41122 and a main-partition memory region 41133 (described later). The software resources distributed to the main partition include a second OS and at least one of a device driver, middleware, and an application that operate on the second OS.

Here, the first OS and the second OS are realized by an OS that has a structure in which a plurality of OSes (such as a plurality of types of OSes or one type of OS that can be provided with a plurality of OS instances) can be arranged on one control device such as the many-core processor 4112, and are realized by, for example, eMCOS of eSOL Co., Ltd.®.

The resetting unit 41125 resets resources distributed to a partition in which a problem has been detected by the problem detector 41124. Resources distributed to one partition are independent of resources distributed to another partition, and the resetting unit 41125 can reset resources distributed to each partition for each partition.

The memory 4113 is, for example, a DDR SDRAM (double-data-rate synchronous dynamic random access memory), and includes the secure-partition memory region 41131, the shared memory region 41132, and the main-partition memory region 41133.

The secure-partition memory region 41131 is a memory region that is distributed to the secure partition by the system controller 412 performing the initial setting and used by the secure partition unit 41121.

The shared memory region 41132 is a memory region that is used by the communication unit 41123.

The main-partition memory region 41133 is a memory region that is distributed to the main partition by the system controller 412 performing the initial setting and used by the main partition unit 41122.

In the video signal processing unit 411 having the configuration illustrated in FIG. 2, a video signal is processed by the display video signal processing in a normal state, in order of arrow A, arrow B, arrow C, arrow D, arrow E, and arrow F in FIG. 2. In other words, in this case, processing is performed by both the secure partition unit 41121 and the main partition unit 41122.

On the other hand, for example, when a problem has occurred with a resource distributed to the main partition, a video signal is processed by the display video signal processing performed, in order of arrow A, arrow B, arrow E, and arrow E in FIG. 2 excluding arrow C and arrow D in FIG. 2, from the problem detector 41124 detecting the problem to the resetting unit 41125 performing a resetting so that the resource returns to normal. In other words, in this case, processing of the secure partition unit 41121 is performed, but processing of the main partition unit 41122 is not performed. Then, after the resource with which the problem has occurred has been reset by the resetting unit 41125 and returned to normal, the display video signal processing returns to a normal state.

This change in display video signal processing is performed according to an anomaly monitoring operation (described later) (an operation that monitors an anomaly in the video signal processing unit 411) performed in the endoscopic system 1.

In the endoscopic system 1 that includes the video signal processing unit 411 having the configuration described above, the video signal processing unit 411 is an example of a video signal processing unit that processes a video signal input from an endoscope. A portion of the functions of the system controller 412 are an example of a distribution unit that distributes hardware resources and software resources related to video signal processing performed by the video signal processing unit to a first partition and a second partition. Another portion of the functions of the system controller 412 are an example of a first assignment unit that assigns minimal processing from among the video signal processing to the resources distributed to the first partition. Yet another portion of the functions of the system controller 412 are an example of a second assignment unit that assigns processing from among the video signal processing that is other than the minimal processing to the resources distributed to the second partition. The problem detector 41124 is an example of a monitoring unit that monitors anomalies in the resources distributed to the first partition and the second partition. The resetting unit 41125 is an example of a resetting unit that only resets resources distributed to a partition in which an anomaly has been detected by the monitoring unit.

Figure 3:
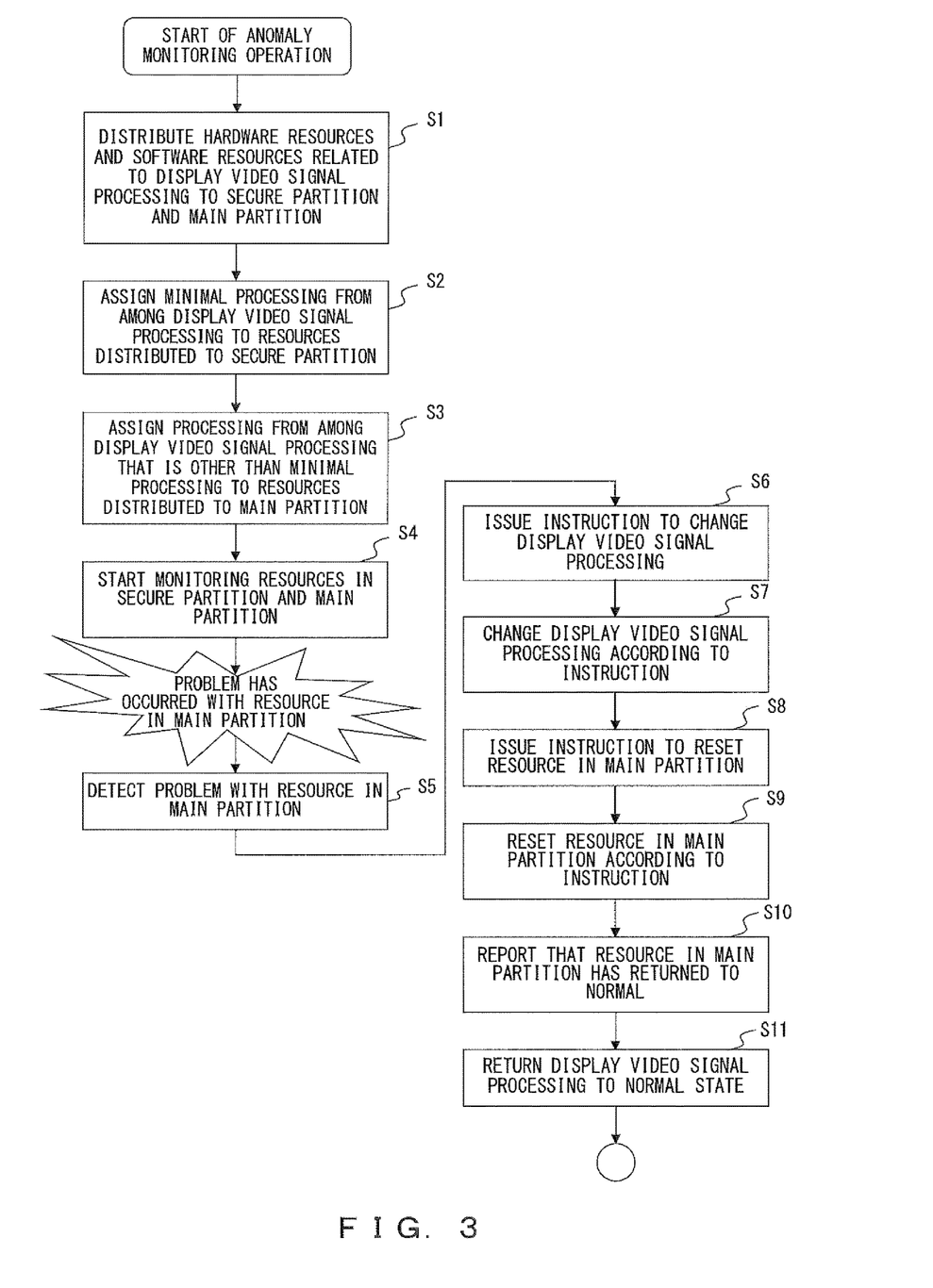
FIG. 3 is a flowchart that illustrates an example of an anomaly monitoring operation (an operation for monitoring an anomaly in the video signal processing unit) according to the embodiment.

FIG. 3 is a flowchart that illustrates an example of an anomaly monitoring operation performed in the endoscopic system 1.

As illustrated in FIG. 3, in this operation, first, the system controller 412 performs an initial setting of the video signal processing unit 411 (S1 to S3). Specifically, the system controller 412 distributes hardware resources and software resources related to display video signal processing performed by the video signal processing unit 411 to the secure partition and the main partition (S1), assigns minimal processing from among the display video signal processing to the resources distributed to the secure partition (S2), and assigns processing from among the display video signal processing that is other than the minimal processing to the resources distributed to the main partition (S3). In addition, for example, processing of distributing cores included in the many-core processor 4112 to the partition for communication, the partition for problem detection, and the partition for resetting is also performed in the initial setting performed by the system controller 412.

When the initial setting of the video signal processing unit 411 has been completed as described above, the problem detector 41124 starts monitoring the hardware resources and the software resources distributed to the secure partition and the hardware resources and the software resources distributed to the main partition (S4).

After S4, when a problem has not occurred with any of the resources distributed to the secure partition or with any of the resources distributed to the main partition, a video signal is processed in order of arrow A, arrow B, arrow C, arrow D, arrow E, and arrow F in FIG. 2 (that is, processing is performed by both the secure partition unit 41121 and the main partition unit 41122). In this case, the display video signal processing in a normal state is performed, and a video according to this processing is displayed on the monitor 43.

On the other hand, after S4, for example, when a problem (such as an exception process) has occurred with a resource distributed to the main partition and the problem detector 41124 has detected the problem, the following processing is performed.

First, when the problem detector 41124 has detected the problem (S5), the problem detector 41124 instructs the secure partition unit 41121 through the communication unit 41123 to change the display video signal processing such that a video signal is processed in order of arrow A, arrow B, arrow E, and arrow F in FIG. 2 excluding arrow C and arrow D in FIG. 2 (that is, processing is performed only by the secure partition unit 41121, from among the secure partition unit 41121 and the main partition unit 41122) (S6). This instruction also includes a report that a problem has occurred with the resource distributed to the main partition.

Next, the secure partition unit 41121 changes the display video signal processing according to the instruction (S7). As a result, a video that corresponds to the display video signal processing after the change (display video signal processing in which a video signal is processed in order of arrow A, arrow B, arrow E, and arrow E in FIG. 2 excluding arrow C and arrow D in FIG. 2) is displayed on the monitor 43.

Next, the secure partition unit 41121 instructs the resetting unit 41125 through the communication unit 41123 to reset the resource distributed to the main partition (S8).

Next, the resetting unit 41125 resets the resource distributed to the main partition according to the instruction (S9). The resources distributed to the secure partition and the resources distributed to the main partition are independent of each other, so the resetting of the resource distributed to the main partition will not affect any of the resources distributed to the secure partition.

After that, when the resource distributed to the main partition has returned to normal by the resetting unit 41125 performing the resetting, the main partition unit 41122 reports to the secure partition unit 41121 through the communication unit 41123 that the resource distributed to the main partition has returned to normal (S10).

Next, when the secure partition unit 41121 has received the report, the secure partition unit 41121 returns the display video signal processing to the normal state (S11). As a result, a video that corresponds to the display video signal processing in the normal state (the display video signal processing in which a video signal is processed in order of arrow A, arrow B, arrow C, arrow D, arrow E, and arrow F in FIG. 2) is displayed on the monitor 43.

According to the above-described anomaly monitoring operation illustrated in FIG. 3, even if a problem has occurred with a resource distributed to the main partition, for example, during an endoscopic examination, it is possible to solve the problem that occurs with the resource distributed to the main partition while keeping a video displayed on the monitor 43, wherein the video display is not allowed to be stopped during the endoscopic examination.

Alternatively, when the structure in which a video signal input from the imaging element 24 is processed and output to the monitor 43 is regarded as one system in the video signal processing unit 411 illustrated in FIG. 2, it can also be said that, even if a problem has occurred with a resource distributed to the main partition of the system, it is possible to solve the problem without stopping the system, which results in being able to ensure the high availability needed for a medical system such as the endoscopic system 1.

As described above, according to the present embodiment, even if an anomaly has occurred in a hardware resource or a software resource related to the display video signal processing performed by the video signal processing unit 411 that processes a video signal input from the imaging element 24 of the endoscope 2, it is possible to correct the anomaly while ensuring the availability of the video signal processing unit 411.

The following modification may also be made to the present embodiment.

For example, resources similar to those distributed to the secure partition are provided as resources distributed to an alternative secure partition, and when the problem detector 41124 has detected a problem with a certain resource distributed to the secure partition, the resources distributed to the alternative secure partition may perform the processing on behalf of the resources distributed to the secure partition until the problem is solved. In this case, the problem with the certain resource distributed to the secure partition is solved by the resetting unit 41125 resetting the certain resource. Then, after the problem has been solved, the resources distributed to the secure partition may restart performing the processing. According to this modification, even if a problem has occurred with a resource distributed to the secure partition, it is possible to solve the problem that has occurred with the resource distributed to the secure partition while keeping a video displayed on the monitor 43.

The embodiments described above are just examples to facilitate understanding of the present invention, and the invention is not limited to these embodiments. Various modifications and alterations may be made hereto without departing from the spirit of the invention specified in the claims.

What is claimed is:

1. A video processor comprising:
a video signal processing unit that processes a video signal input from an endoscope;
a distribution unit that distributes hardware resources and software resources related to video signal processing performed by the video signal processing unit to a first partition and a second partition;
a first assignment unit that assigns minimal processing from among the video signal processing to the resources distributed to the first partition;
a second assignment unit that assigns processing from among the video signal processing that is other than the minimal processing to the resources distributed to the second partition;
a monitoring unit that monitors anomalies in the resources distributed to the first partition and the second partition; and
a resetting unit that only resets resources distributed to a partition in which an anomaly has been detected by the monitoring unit, wherein
when an anomaly in a certain resource distributed to the second partition has been detected by the monitoring performed by the monitoring unit, the video signal processing unit only performs the minimal processing from among the video signal processing that has been assigned to the resources distributed to the first partition until the certain resource returns to normal by the resetting unit performing the resetting.

2. The video processor according to claim 1, wherein when the certain resource has returned to normal by the resetting unit performing the resetting, the video signal processing unit performs the minimal processing from among the video signal processing and processing from among the video signal processing that is other than the minimal processing, and
the minimal processing has been assigned to the resources distributed to the first partition and the processing other than the minimal processing has been assigned to resources distributed to the second partition.

3. The video processor according to claim 1, wherein the resources distributed to the first partition include one or more core processors distributed for the first partition and a memory region distributed for the first partition as hardware resources, and an operating system distributed for the first partition and at least one of a device driver, middleware, and an application that are distributed for the first partition as software resources; and
the resources distributed to the second partition include one or more core processors distributed for the second partition and a memory region distributed for the second partition as hardware resources, and an operating system distributed for the second partition and at least one of a device driver, middleware, and an application that are distributed for the second partition as software resources.

4. A video processor for use with an endoscope, the video processor comprising:
a processor programmed to:
process a video signal input received from the endoscope;
distribute hardware resources and software resources to a first partition and a second partition for processing of the video signal input;
assign minimal processing from among the video signal processing to the resources distributed to the first partition;
assign processing from among the video signal processing that is other than the minimal processing to the resources distributed to the second partition;
detect whether anomalies are present in the resources distributed to the first partition and the second partition;
reset resources distributed to the first partition or the second partition only when an anomaly has been detected in the respective first partition or the second partition; and
when an anomaly in a certain resource distributed to the second partition has been detected, the minimal processing from among the video signal processing that has been assigned to the resources distributed to the first partition is only performed until the certain resource returns to normal in response to the resetting of resources in the second partition.

5. The video processor according to claim 4, wherein when the certain resource has returned to normal, the minimal processing from among the video signal processing and processing from among the video signal processing that is other than the minimal processing are performed, and
the minimal processing has been assigned to the resources distributed to the first partition and the processing other than the minimal processing has been assigned to resources distributed to the second partition.

6. The video processor according to claim 4, wherein the resources distributed to the first partition include one or more core processors distributed for the first partition and a memory region distributed for the first partition as hardware resources, and an operating system distributed for the first partition and at least one of a device driver, middleware, and an application that are distributed for the first partition as software resources; and the resources distributed to the second partition include one or more core processors distributed for the second partition and a memory region distributed for the second partition as hardware resources, and an operating system distributed for the second partition and at least one of a device driver, middleware, and an application that are distributed for the second partition as software resources.

* * * * *